US012589224B2

(12) United States Patent
DeLorenzo et al.

(10) Patent No.: US 12,589,224 B2
(45) Date of Patent: Mar. 31, 2026

(54) LOW PROFILE ACCESS SHEATHS

(71) Applicant: ABIOMED, Inc., Danvers, MA (US)

(72) Inventors: Charles DeLorenzo, Danvers, MA
(US); Christopher Korkuch, Danvers,
MA (US); Glen Fantuzzi, Danvers, MA
(US); Brian Chouinard, Danvers, MA
(US); Megan Boyd, Danvers, MA (US);
Mithun Rajaram, Danvers, MA (US);
Matthew D'Agostino, Danvers, MA
(US)

(73) Assignee: ABIOMED, INC., Danvers, MA (US)

( * ) Notice: Subject to any disclaimer, the term of this
patent is extended or adjusted under 35
U.S.C. 154(b) by 722 days.

(21) Appl. No.: 17/974,938

(22) Filed: Oct. 27, 2022

(65) Prior Publication Data

US 2023/0134876 A1 May 4, 2023

Related U.S. Application Data

(60) Provisional application No. 63/413,098, filed on Oct.
4, 2022, provisional application No. 63/272,750, filed
on Oct. 28, 2021.

(51) Int. Cl.
*A61M 25/06* (2006.01)
*A61M 25/00* (2006.01)

(52) U.S. Cl.
CPC ........ *A61M 25/06* (2013.01); *A61M 25/0097*
(2013.01); *A61M 2025/0681* (2013.01)

(58) Field of Classification Search
CPC .............. A61M 25/0043; A61M 25/00; A61M
25/0023; A61M 25/0021; A61M 25/0097;
A61M 25/0662; A61M 2025/0681; A61M
25/06
See application file for complete search history.

(56) References Cited

U.S. PATENT DOCUMENTS

| | | | |
|---|---|---|---|
| 3,123,072 A | | 3/1964 | Bellamy et al. |
| 4,840,622 A | * | 6/1989 | Hardy ............... A61M 25/0662 |
| | | | 604/524 |

(Continued)

FOREIGN PATENT DOCUMENTS

| | | |
|---|---|---|
| JP | 2010000351 A | 1/2010 |
| JP | 2011520522 A | 7/2011 |
| WO | 2018092386 A | 5/2018 |

OTHER PUBLICATIONS

English Translation of Japanese Notice of Refusal for corresponding
JP Application No. 2024-525236, dated Apr. 7, 2025.

(Continued)

*Primary Examiner* — Rebecca E Eisenberg
(74) *Attorney, Agent, or Firm* — Meagher Emanuel Laks
Goldberg & Liao, LLP

(57) ABSTRACT

A system for insertion into a vasculature of a patient is
disclosed. The system utilizes a primary tubular sheath body
coupled to a distal portion of an intermediate tubular sheath
body, and a hub coupled to a proximal portion of the
intermediate tubular sheath. The hub may be couplable to a
dilator via an interaction between a dilator cap and the hub,
and the hub may contain a hemostatic valve with a foam
member having one or more visibly identifiably regions.

15 Claims, 9 Drawing Sheets

(56)                    References Cited

U.S. PATENT DOCUMENTS

| | | | | |
|---|---|---|---|---|
| 4,846,812 | A * | 7/1989 | Walker .............. | A61M 25/0662 |
| | | | | 600/581 |
| 5,658,263 | A * | 8/1997 | Dang ............... | A61M 25/0041 |
| | | | | 604/525 |
| 6,325,790 | B1 * | 12/2001 | Trotta ................... | A61L 29/049 |
| | | | | 600/433 |
| 6,488,662 | B2 * | 12/2002 | Sirimanne ......... | A61M 25/0606 |
| | | | | 604/164.01 |
| 2002/0072712 | A1 * | 6/2002 | Nool ................ | A61M 25/0136 |
| | | | | 604/164.08 |
| 2002/0077600 | A1 * | 6/2002 | Sirimanne ......... | A61M 25/0606 |
| | | | | 606/198 |
| 2009/0287182 | A1 | 11/2009 | Bishop et al. | |
| 2009/0287183 | A1 * | 11/2009 | Bishop .............. | A61M 25/0662 |
| | | | | 604/509 |
| 2009/0312786 | A1 | 12/2009 | Trask et al. | |
| 2017/0056633 | A1 | 3/2017 | Aman et al. | |
| 2018/0256859 | A1 * | 9/2018 | Korkuch ............. | A61M 25/005 |
| 2020/0367929 | A1 | 11/2020 | Ginn et al. | |
| 2021/0252217 | A1 | 8/2021 | Fischer, Jr. et al. | |
| 2022/0152367 | A1 * | 5/2022 | Gafoor .............. | A61M 25/0662 |
| 2023/0233802 | A1 * | 7/2023 | Finck ................... | A61M 60/113 |

OTHER PUBLICATIONS

International Search Report and Written Opinion for corresponding PCT application No. PCT/US2022/048042, dated Mar. 22, 2023.

* cited by examiner

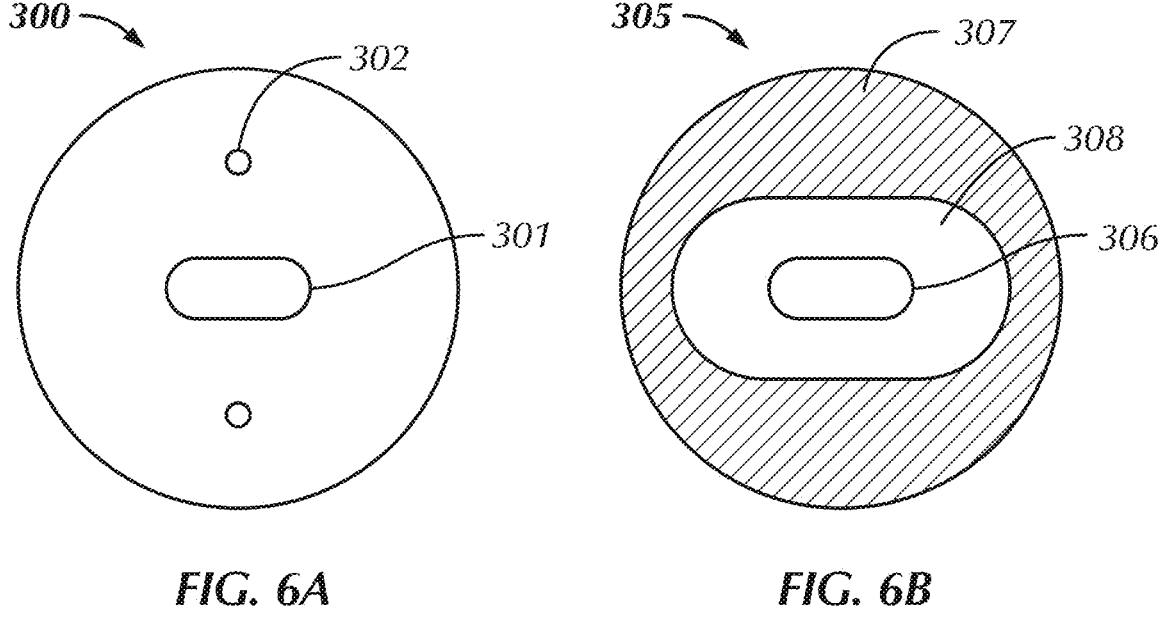
FIG. 6A
FIG. 6B
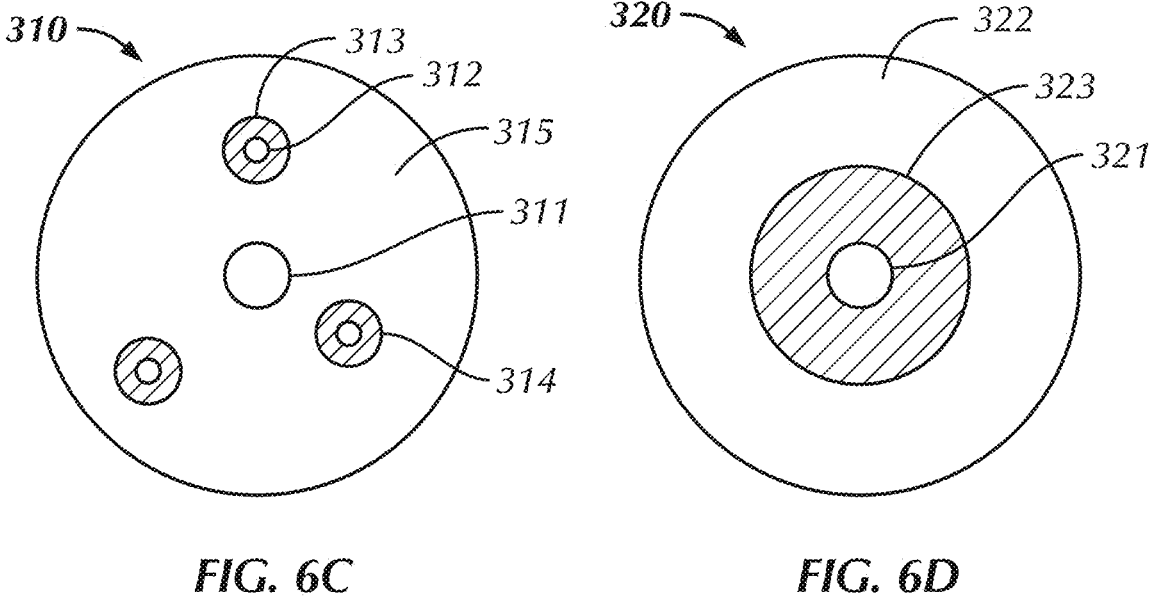
FIG. 6C
FIG. 6D

LOW PROFILE ACCESS SHEATHS

CROSS-REFERENCE TO RELATED APPLICATIONS

The present application claims priority to U.S. Provisional Patent App. Nos. 63/272,750, filed 28 Oct. 2021, and 63/413,098, filed 4 Oct. 2022, the entire contents of each of which are incorporated by reference herein.

TECHNICAL FIELD

The present disclosure is directed to non-peel away introducer sheath assemblies and dilator assemblies that may permit the introduction of one or more medical devices into a patient at a single insertion site, such introducer sheath assemblies having a hemostatic valve to reduce or eliminate the discharge of body fluids from the patient through the insertion site of an introducer sheath assembly.

BACKGROUND

A mechanical circulatory support device (e.g., an intracardiac heart pump assembly) or other medical devices, can be introduced into a patient in various ways. A common approach is to introduce the device through the vascular system either surgically or percutaneously during a cardiac procedure. If the medical device is expected to remain in the patient for an extended period of time, typically utilized peel-away introducer sheaths may be peeled away and replaced with a smaller diameter sheath preinstalled on the medical device (e.g., a repositioning sheath), to reduce the risk of blockages in the bloodstream.

BRIEF SUMMARY

A first aspect is drawn to a device for insertion into a vasculature of a patient, where the device comprises a primary tubular sheath body, an intermediate tubular sheath body connected to a proximal end of the primary tubular sheath body, and a hub connected to a proximal portion of the intermediate tubular sheath body. The primary tubular sheath body is comprised of a first material, the intermediate tubular sheath body is comprised of a second material, and the hub is comprised of a third material, where a theoretical interfacial bonding strength between the first and second material, and a theoretical interfacial bonding strength between the third material and the second material, are both greater than a theoretical interfacial bonding strength between the first material and the third material.

In some embodiments, the intermediate tubular sheath body may have a first inner diameter at its distal end, and a second inner diameter at an axial distance proximal to the distal end, the second inner diameter being greater than the first inner diameter. In some embodiments, the second inner diameter may be between 5 mm and 6 mm.

In some embodiments, the first material may comprise a polyether block amide (PEBA). In some embodiments, the second material may comprise a thermoplastic styrene-butadiene copolymer. In some embodiments, the third material may comprise acrylonitrile butadiene styrene.

In some embodiments, the primary tubular sheath body may comprise a plurality of layers. These layers may include, e.g., a frame layer and an outer jacket. In some embodiments, the frame layer may comprise nitinol, and the outer jacket may comprise a polyether block amide (PEBA).

In some embodiments, the device may include a sideport extending from the hub.

In some embodiments, the hub may comprise a rotatable portion that is rotatable relative to the hub, the primary tubular sheath body, and the intermediate tubular sheath body, the rotatable portion being connected to a distal portion of the hub. In some embodiments, the rotatable portion may be rotatable (i.e., capable of being rotated) by at least 180 degrees. In some embodiments, the rotatable portion may be rotatable by at least 360 degrees. In some embodiments, the rotatable portion may be configured to allow a sideport extending from the hub to lie flat against a patient. In some embodiments, the rotatable portion may comprise a butterfly, a suture pad, or a combination thereof.

A second aspect is drawn to an apparatus comprising a hub, a sheath with a tubular sheath body operably coupled to the hub, a dilator having a dilator body receivable through the tubular sheath body, a dilator hub coupled to a proximal end of the dilator body, and a dilator handle coupled to the dilator cap. The hub includes one or more threads extending partially around circumference of hub, each thread having a locking portion that has a different axial thickness than a different portion of the thread. The tubular sheath body extending from a proximal end to a distal end, the proximal end operably coupled to the hub, and the dilator cap includes a groove or channel configured to receive the thread when the dilator is received through the sheath body, the groove or channel configured to have a ridge or depression adapted to engage with the locking portion of the thread.

In some embodiments, the groove or channel may be configured to have a ridge and the locking portion has a smaller axial thickness than that a different portion of the thread. In some embodiments, a height of the ridge or depression may be the same as a difference in the axial thickness between the locking portion and the different portion.

In some embodiments, the hub and the dilator cap may each contain an indicator on an external surface configured to convey when the groove or channel is aligned with the thread prior to being locked into position.

In some embodiments, the dilator cap may define an opening extending from a proximal surface to a distal surface along a central axis, the opening having a central circular portion and one or more spokes extending outward from the central circular portion, each spoke configured to align with a ridge on a distal surface of the dilator handle.

In some embodiments, the apparatus is configured to provide an indicium to a user that the dilator is locked into place, such as an auditory sound, a vibration through the dilator handle, or a combination thereof.

A third aspect is drawn to a hemostatic valve assembly, comprising a foam member configured to secure an elastomeric member at least partially within a housing and provide structural support against a proximal end of the elastomeric member, the foam member having a proximal surface defining a first opening extending along a longitudinal axis from the proximal surface to a distal surface a longitudinal axis of the hemostatic valve assembly, and the foam member having at least one visibly identifiable portion a predetermined distance from at least one edge of the first opening.

In some embodiments, the foam may contain a silicone oil. In some embodiments, the first opening may be laser cut.

In some embodiments, the at least one visibly identifiable portion may comprise one or more additional openings extending at least partially from the proximal surface towards the distal surface. In some embodiments, each of the one or more additional openings may be equidistant from the at least one edge. In some embodiments, each of the one or more additional openings may have a diameter less than 0.5 mm. In some embodiments, the one or more additional openings may comprise between 2 and 4 additional openings.

In some embodiments, the at least one visible identifiable portion may comprise a portion that is visibly darker or lighter than a different portion of the foam.

BRIEF DESCRIPTION OF DRAWINGS

FIGS. 6A-6D are 2D representations of different embodiments of the foam member.

DETAILED DESCRIPTION

For mechanical circulatory support devices, peel-away introducer sheaths may be used when the device is expected to remain in a patient for an extended period of time (e.g., by peeling away the introducer sheath and replacing it with a smaller diameter sheath preinstalled on the medical device). However, as it becomes more desirable to utilize a single point of insertion into the body to introduce multiple medical devices, peel-away introducers may become less desirable due to the intentionally reduced sidewall strength of such introducers. Additionally, typical peel-away introducers have a large outer diameter, which can undesirably obstruct blood flow past the introducer and lead to lower limb ischemia.

Thus, the inventors have appreciated that a low-profile non-peel away introducer sheath may be desirable. However, to maintain the desirable features of such sheaths, further changes to the design may be required, as the dimensions cannot simply be reduced proportionally and remain useable and manufacturable.

To that end, a low-profile non-peel away introducer sheath assembly, and dilator assemblies that enable such sheaths to be useful, that incorporate design features that allow the benefits of current non-peel away introducer sheaths while remaining manufacturable are desirable.

Figure 1A:
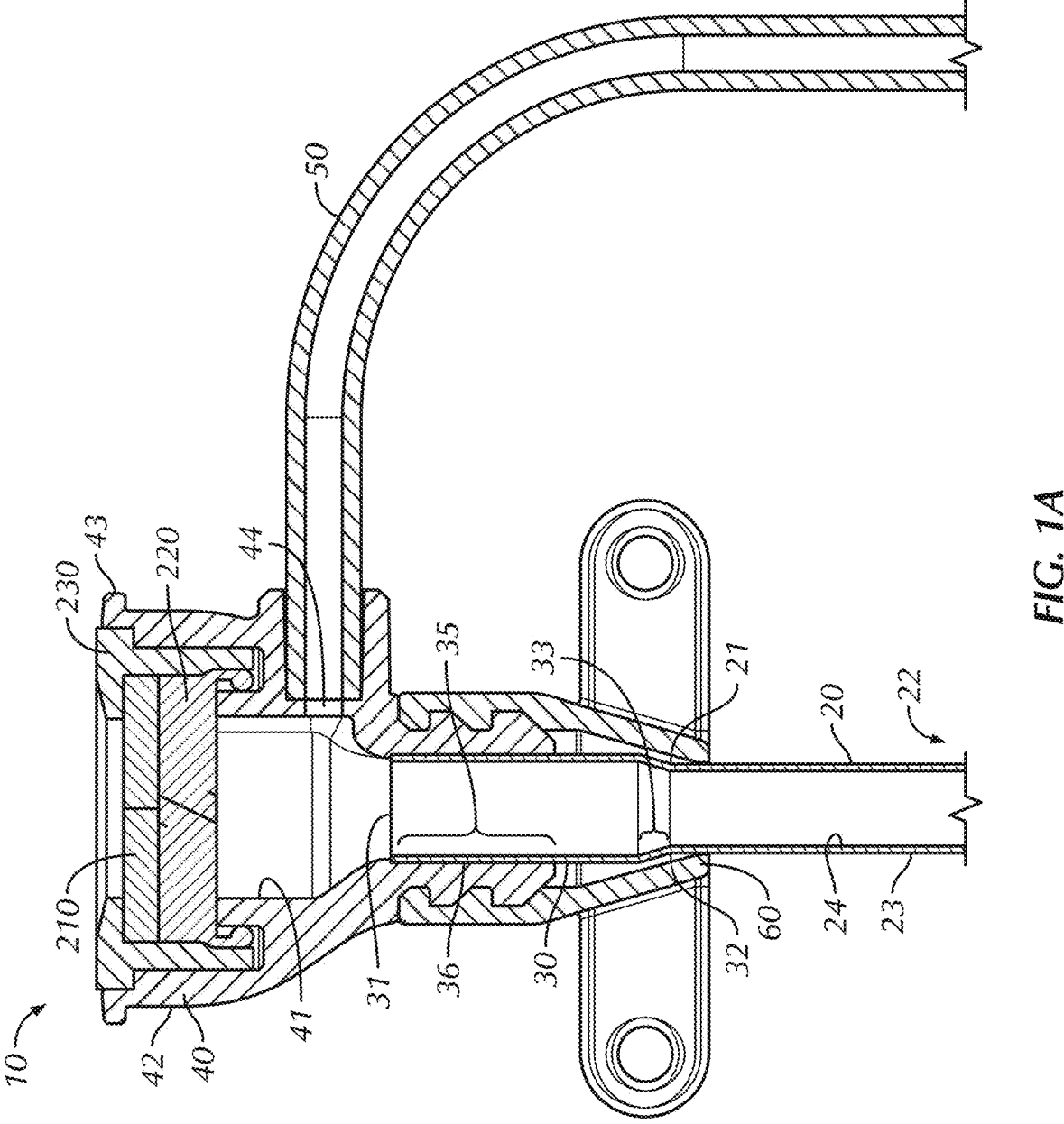
FIG. 1A is a 2D schematic of an embodiment of an introducer sheath with a hemostatic valve.
Figure 1B:
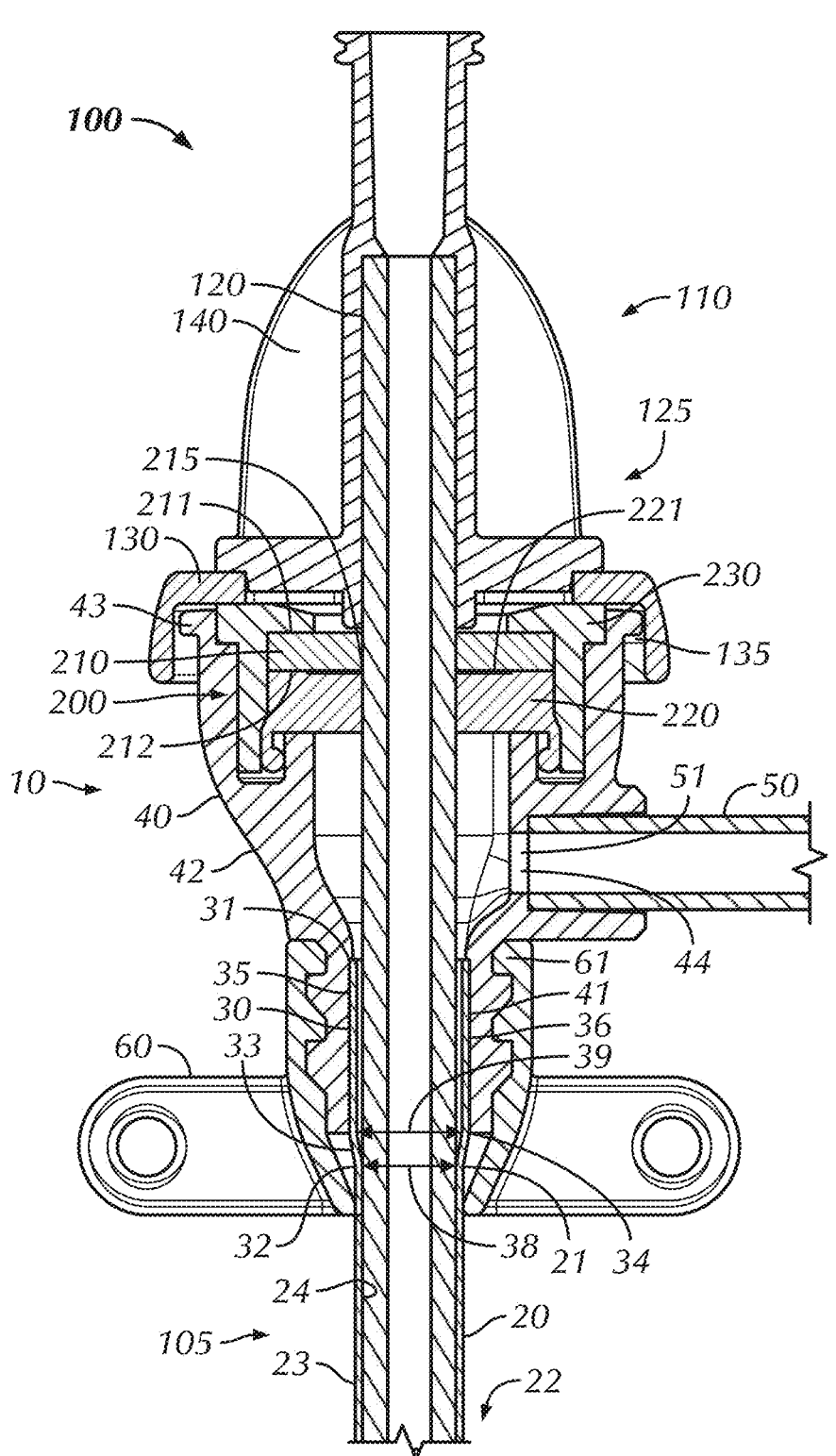
FIG. 1B is a 2D schematic of an embodiment of an introducer sheath with a hemostatic valve and a dilator assembly inserted.

As seen in FIGS. 1A and 1B, a system for insertion into the vasculature of a patient can be seen. The system generally comprises a hub 40 operably connected to a sheath 105, the hub comprising a hemostatic valve 200 through which, e.g., a dilator assembly 110, a heart pump, or other medical devices may be inserted.

A first aspect of the present disclosure is drawn to a device 10 for insertion into a vasculature of a patient can be seen. The device 10 may include a primary tubular sheath body 20 coupled to a distal end of an intermediate tubular sheath body 30, and a hub 40 coupled to a proximal portion of the intermediate tubular sheath body 30. The hub 40 may be connected to a sideport 50. A rotatable portion 60 or member may be operably coupled to a distal end of the hub.

Primary Tubular Sheath Body

The primary tubular sheath body 20 may include a first material, and the primary tubular sheath body may extend from a proximal end 21 to a distal end 22.

In some embodiments, the first material may comprise a polyether block amide (PEBA), such as the PEBAX® elastomers sold by Arkema.

In some embodiments, the primary tubular sheath body 20 may comprise a plurality of layers. In some embodiments, the primary tubular sheath body 20 may comprise an outer jacket 23 (which may comprise or consist of a PEBA), and an inner frame layer 24 (which may comprise or consist of nitinol).

Intermediate Tubular Sheath Body

The device also may include an intermediate tubular sheath body 30 (see FIGS. 1A and 1B) comprising or consisting of a second material, the intermediate sheath body extending from a proximal end 31 to a distal end 32. The distal end 32 of the intermediate tubular sheath body 30 may be connected to the proximal end 21 of the primary tubular sheath body 20. In some embodiments, the distal end of the intermediate tubular sheath body may be butt welded to the proximal end of the primary tubular sheath body, though it should be understood that other types of joints between the primary and intermediate tubular sheath bodies may be suitable.

In some embodiments, the intermediate tubular sheath body 30 may comprise or consist of a thermoplastic styrene-butadiene copolymer, such as the STYROLUX® resins sold by Entec Polymers.

In some embodiments, the intermediate tubular sheath body 30 may have a proximal portion 35 with a constant inner diameter 39 and a distal portion 33 that necks down linearly from the inner diameter 39 of the proximal portion to a smaller inner diameter 38 at the distal end 32. In some embodiments, the intermediate tubular sheath body may have a first inner diameter 38 at the distal end 32, and a second inner diameter 39 at an axial distance proximal to the distal end 34. In some embodiments, the second inner diameter 39 may be greater than the first inner diameter. In some embodiments, the second inner diameter 39 is between 5 mm and 6 mm. In some embodiments, this inner diameter may be the same as the inner diameter of the primary tubular sheath.

Hub

The device also may comprise a hub 40 (see, e.g., FIG. 1A). The hub may comprise or consist of a third material, and the hub 40 may be connected to a proximal portion 35 of the intermediate sheath body 30 and be separated from the primary tubular sheath body 20 by the intermediate tubular sheath body 30.

In some embodiments, the third material may be acrylonitrile butadiene styrene.

In some embodiments (see, e.g., FIGS. 1A and 1B), an inner surface 41 of the hub 40 may be connected to a portion of the outer surface 36 of the intermediate tubular sheath body 30 and not connected with the primary tubular sheath body 20. In some embodiments, the hub is only connected to the proximal portion 35 of the intermediate tubular sheath body 30 with a constant diameter 39 and is not connected to the distal portion 33 that necks down to a smaller inner diameter.

Because different properties are needed for the hub than for the primary tubular sheath body, the materials that comprise each of these parts are necessarily different, and these differences often result in the two components not being able to bond the components together effectively. Thus, in some embodiments, the intermediate layer aids in bonding by having an intermediate layer that the two components bond to more effectively than each other. Therefore, in the present disclosure, the first material, second material, and third material may be configured such that a theoretical interfacial bonding strength between the first and second material, and a theoretical interfacial bonding strength between the third material and the second material, are both greater than a theoretical interfacial bonding strength between the first material and the third material. As is known in the art, Interfacial bonding strength (IBS) is the strength that bonds two layers at the interface, and can be tested via, e.g., tensile tests or shear tests, although tensile is more typically utilized.

Sideport

As also shown in FIGS. 1A and 1B, the device may also comprise a sideport 50 extending from the hub 40. A first end 51 of the sideport 50 may be connected an entrance 44 defined by an exterior surface 42 of the hub 40 that extends to the interior surface 41 of the hub 40.

Rotatable Portion

The device may also comprise a rotatable portion 60 (see e.g., FIG. 1A) that is rotatable around a central axis relative to the primary tubular sheath body 20. In some embodiments, the intermediate tubular sheath body 30, the hub 40, and the rotatable portion may be connected to a distal portion of the hub 40.

In some embodiments, the rotatable portion 60 may be attached in a non-removable (or not easily removable) fashion, such as via a plurality of snap-fit joints 61. In some embodiments, the rotatable portion may comprise a butterfly, a suture pad, or a combination thereof.

In some embodiments, the rotatable portion 60 may be rotatable around a central axis (in FIGS. 1A and 1B, the central axis being the centerline of the primary tubular sheath body 20 and the intermediate tubular sheath body 30) by at least 180 degrees. For example, in some embodiments, the rotatable portion (when attached to a patient) can still allow the hub to be rotated such that (at a minimum) the sideport can face towards the right side of the patient or towards the left side of the patient. In some embodiments, the rotatable portion 60 may be rotatable around a central axis by at least 360 degrees, up to and including being freely rotatable without restriction.

In some embodiments, the rotatable portion 60 may be configured to allow the sideport 50 extending from the hub 40 to lie substantially flat against a patient, regardless of the orientation of the rotatable portion 60 on the body of the patient. For example, in some embodiments, by allowing the hub to be rotated such that the entrance 44 of the hub where the .sideport 50 is connected to is directed towards a patient's body (or at least, not be directed away from the patient's body), the sideport can readily lie substantially flat against a patient.

In some embodiments, the rotatable portion 60 may be configured to encircle the portion of the device 10 where some or all of the intermediate tubular sheath body 30 is positioned, as well as encircling the point of connection between the primary tubular sheath body 20 and the intermediate tubular sheath body 30 (e.g., encircling at least a portion of the proximal end of the tubular sheath body 20).

Also disclosed is an apparatus (or system) 100. In some embodiments, the apparatus 100 comprises a hub 40, a sheath 105, and a dilator 110.

Hub

Figure 2:
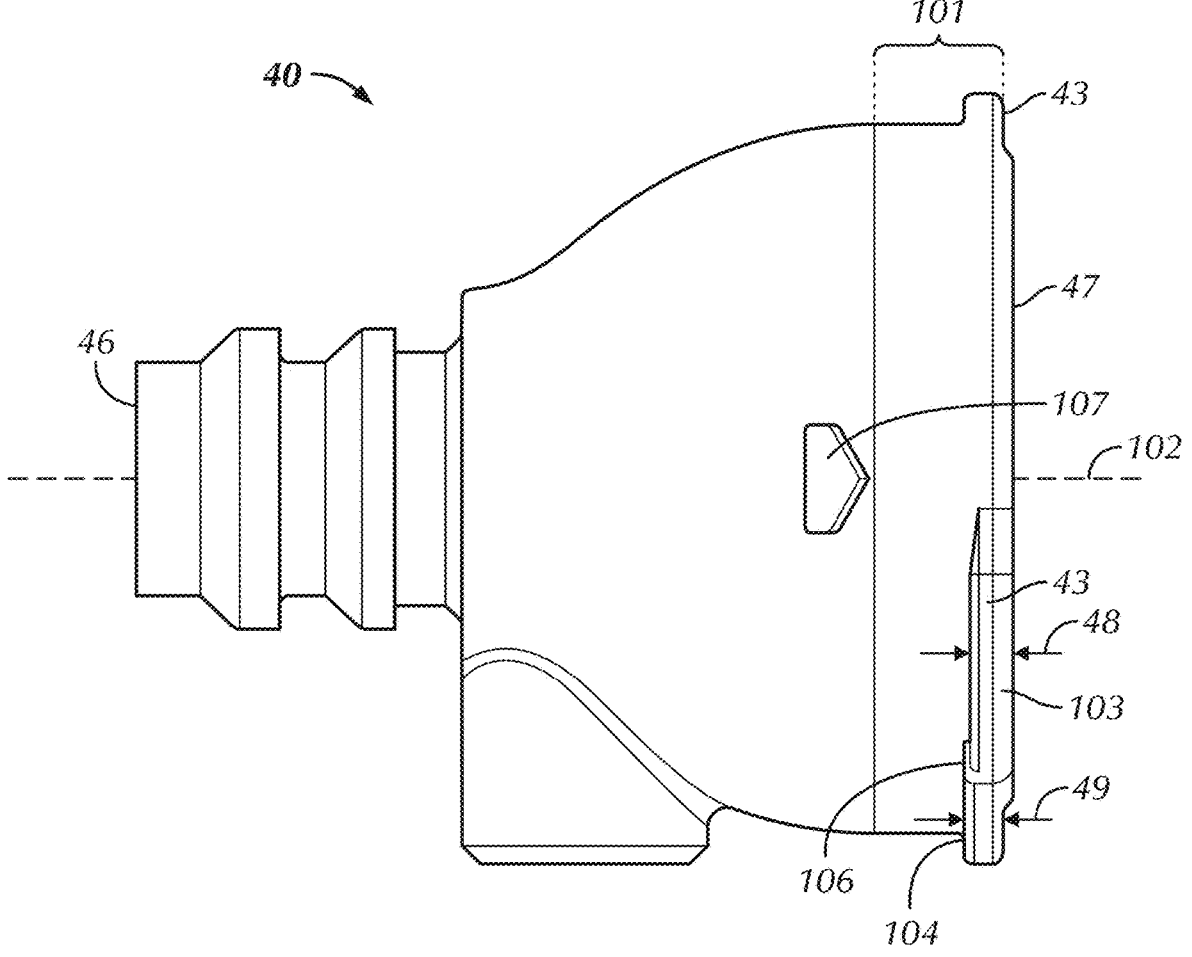
FIG. 2 is a 2D schematic of an embodiment of a hub.

Referring to FIG. 2, a hub 40 can be seen, the hub having a distal end 46 and a proximal end 47. The hub 40 may include one or more threads 43 (two threads are shown in FIG. 2 by way of an example), each thread extending at least partially around the circumference of hub 40. As will be appreciated, the threads may have other suitable arrangements in other embodiments. As shown in FIG. 2, the threads 43 may be disposed in a proximal portion 101 of the hub 40, at or near the proximal end 47.

As shown in FIG. 2, in some embodiments, each thread may have portions with different axial thicknesses (e.g., a thickness of the thread in an axial direction). For example, in one embodiment, each thread 43 may have a first, locking portion 104 with a first axial thickness 49 that may be different than a second axial thickness 48 in a second portion 103 of each thread 43.

In some embodiments, the locking portion 104 may have first axial thickness 49 that is less than the second axial thickness 48 of the second portion 103. In some embodiments, the locking portion 104 may have first axial thickness 49 that is greater than the second axial thickness 48 of the second portion 103.

In some embodiments, each thread may have one locking portion 104 and one second portion 103. In some embodiments, each thread may have one locking portion 104 and two second portions 103 (one on each side of the locking portion).

In some embodiments, the interface 109 of the locking portion 104 and the second portion 103 may extend in a non-radial direction. In some embodiments, the interface 109 of the locking portion 104 and the second portion 103 may extend in a radial direction.

The hub 40 may also comprise an indicator 107, such as a shape or design molded or etched into or onto an outer surface of the hub, to aid in aligning the hub 40 and the dilator 110.

Sheath

Referring again to FIG. 1B, the apparatus 100 also may comprise a sheath 105. The sheath 105 may include a primary tubular sheath body 20 extending from a proximal end 21 to a distal end 22. In some embodiments, the proximal end 21 may be operably coupled to the hub 40, such as via an intermediate tubular sheath body 30 as described previously.

Dilator

The apparatus 100 also may include a dilator 110 (see, e.g., FIG. 1B). The dilator 110 may comprise a dilator body 120 receivable through the tubular sheath body 20, and a dilator hub 125 coupled to a proximal portion of the dilator body 120. The dilator hub 125 may comprise or consist of a dilator cap 130 and a dilator handle 140. In some embodiments, the dilator handle 140 may be coupled to a proximal surface of the dilator cap 130.

Figure 3A:
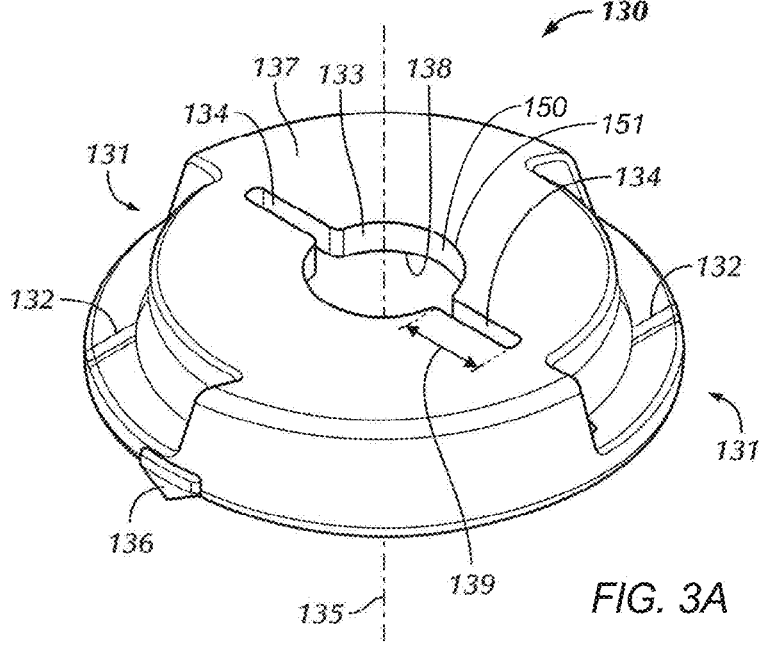
FIGS. 3A and 3B are orthogonal representations of embodiments of dilator caps.

Referring to FIG. 3A, the dilator cap 130 may include at least one groove or channel 131 configured to receive the one or more threads 43 on the hub 40 when the dilator body 120 is received through the primary tubular sheath body 20. In this regard, the size and shape of the at least one groove or channel 131 may correspond to the size and shape of the one or more threads 43 on the hub 40.

In some embodiments, one or more of the grooves or channels 131 may be configured to have a ridge or depression 132 adapted to engage with the locking portion 104 of the thread 43. In some embodiments, every groove or channel 131 may be configured with a ridge or depression 132 adapted to engage with the respective locking portion of the respective thread. In some embodiments, the groove or channel 131 may be configured to have the ridge 132, and the locking portion may a smaller first axial thickness than the second portion of the thread (e.g., to allow for engagement between the ridge or depression and the locking portion).

In some embodiments, the dilator cap 130 may also contain an indicator 136, such as a shape or design molded or etched into or onto an outer surface of the dilator cap 130, to aid in aligning the hub 40 and the dilator 110 (and more specifically, aligning the dilator cap and the hub). In some embodiments, the hub 40 and the dilator cap 130 may each contain an indicator (107, 136) configured to convey when the groove or channel is aligned with the thread prior to being locked into position. In some embodiments, the hub 40 and the dilator cap 130 may each contain an indicator (107, 136) configured to convey when the groove or channel is locked into the locked position. In some embodiments, the dilator cap 130 may contain one indicator (136) and the hub may contain two indicators (107) configured to convey both when the groove or channel is aligned with the thread prior to being locked in the locked position, and also when the groove or channel is locked in the locked position.

The dilator cap 130 may be configured such that any ridge or depression 132 has a height in the axial direction that is equal or substantially equal to the difference in height between the locking portion 104 and the (one or more) second portion 103.

The dilator 110 may be configured to provide an indicium, such as a non-visual indicium, to a user that the dilator is locked into place (e.g., locked onto the hub). By configuring the dimensions and composition of the components, such as the dilator cap 130, the dilator can be configured to, e.g., produce an auditory sound. For example, the dilator cap may produce a noticeable "click" sound, a vibration through the dilator handle, or a combination thereof when the dilator is locked into place. Other indicia may be utilized as appropriate to indicate a locking status of the dilator.

In some embodiments, the dilator cap 130 has a proximal surface 137 that defines an opening 133 extending from the proximal surface 137 to a distal surface 138 of the dilator cap (see, e.g., FIG. 3A). The opening 133 may be circular or substantially circular in shape, and the center of the opening may be aligned with a centerline 135 of the dilator cap 130. In some embodiments, the opening 133 may have a diameter between, e.g., 7 and 8 mm. The proximal surface 137 may also define one or more "spoke" or "wing" channels 134 that extend outwardly from the central opening 133. In this regard, the spoke or wing channels 134 are additional openings defined by the proximal surface and extend from the proximal surface 137 to the distal surface 138.

Figure 3B:
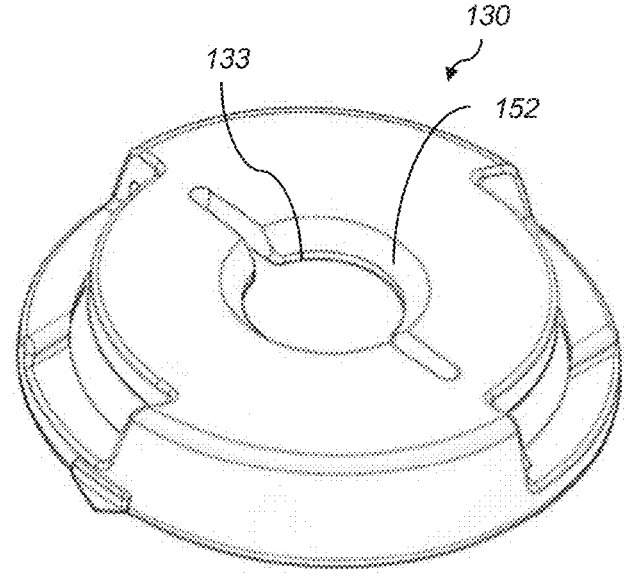

In some embodiments, the central opening 133 may have an inner surface 150 that includes straight-cut sides extending in the axial direction (e.g., parallel to the central axis 135) from the proximal surface 137 to the distal surface 138. In some embodiments, a proximal edge 151 of the inner surface 150 of the central opening may be shaped to ease assembly. Referring to FIG. 3B, the inner surface 150 of the central opening 133 also may include a chamfer 152 at the proximal surface 137 (e.g., at least a portion of the proximal edge may be chamfered). In such embodiments, the inner surface central opening 133 may be rounded at the proximal surface 137 (e.g., at least a portion of the proximal edge may be rounded).

In some embodiments, there may be additional text or images provided on the proximal surface 137. For example, in some embodiments, one or more words or icons are embossed on the proximal surface. In some embodiments, such words or icons provides directions or use instructions to a user (e.g., "twist" or "push"), or information related to the size of the opening of the dilator (e.g., "14F" to indicating the dilator is a 14 French dilator, etc.).

In some embodiments, the spokes or wing channels 134 may help align the dilator handle 140 with the dilator cap 130. In some embodiments, the spokes or wings 134 may aid in transferring force from the handle to the cap, such as when the handle and cap are coupled to one another.

In some embodiments, a single spoke or wing channel 134 may be present. In some embodiments, the distal cap 130 comprises between 2 and 4 spoke or wing channels 134. In some embodiments, the spoke or wing channel 134 are symmetrically arranged around the central opening 133. In some embodiments, each spoke or wing channel 134 may extend radially a same distance 139 from an edge of the central opening 133 towards an outer edge of the proximal surface. In some embodiments, each spoke or wing channel may have the same size and shape. As will be appreciated, the spoke or wing channels may have a size and shape that corresponds to corresponding coupling regions on the dilator handle.

Figure 4:
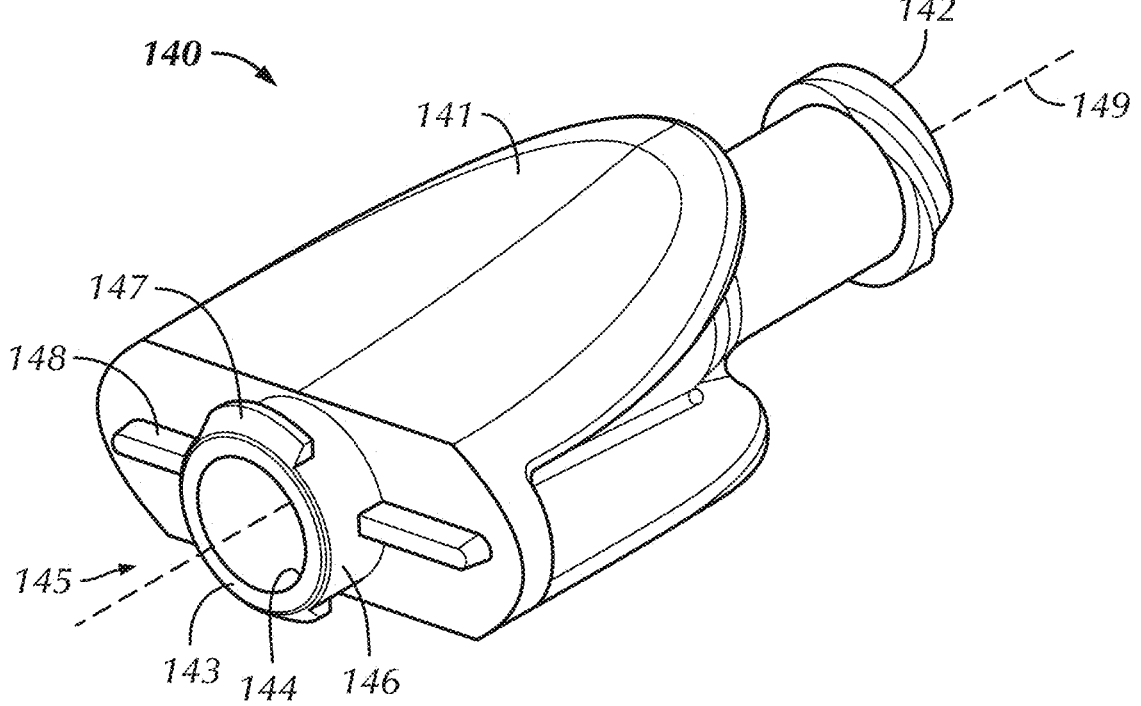
FIG. 4 is an orthogonal representation of an embodiment of a dilator handle.

Referring to FIG. 4, an embodiment of a dilator handle 140 is seen. The dilator handle 140 may include a dilator handle body 141 that has a proximal end 142 and a distal end 143. The dilator handle body 141 may define a central lumen 144 extending from the proximal end 142 to the distal end 143.

In some embodiments, the distal portion of the dilator handle may comprise a coupling portion 145 that is configured to allow the dilator handle 140 to be coupled to the dilator cap 130. In some embodiments, the coupling portion may include one or more locking extensions configured to pass through the central opening and the one or more spoke or wing channels on the dilator cap. For example, in some embodiments, the coupling portion 145 comprises a central extension 146 configured to pass through the central opening 133 on the dilator cap 130. The central extension 146 may comprise one or more locking ridge 147 configured to pass through the central opening 133 and interact with a distal surface 138 of the dilator cap, holding the dilator handle 140 to the dilator cap 130. In some embodiments, the distal surface of the dilator handle may comprise one or more additional spoke or wing extensions 148 configured to extend at least partially into the spoke or wings channels 134 when the dilator handle is connected to the dilator cap. In some embodiments, there are 2-4 additional spoke or wing extensions 148. In some embodiments, each additional spoke or wing extension may connect to a surface of the central extension 146. In some embodiments, each additional spoke or wing extension is configured such that a distal surface of each additional spoke or wing extension 148 is parallel with the distal surface 138 of the distal cap when the dilator handle is connected to the dilator cap. The central axis 149 of the dilator handle 140 may be configured to align with the central axis 135 of the dilator cap 130.

The dilator handle may comprise one or more threads at the proximal end 142 for receiving one or more additional dilator components through the central lumen 144 along the central axis 135.

A third aspect of the present disclosure is a drawn to a hemostatic valve assembly. Referring to FIGS. 1A and 1B, a hemostatic valve assembly 200 is seen. The hemostatic valve assembly generally comprises a foam member 210 configured to secure an elastomeric member 220 at least partially within a housing 230 and provide structural support against a proximal end 221 of the elastomeric member 220.

In some embodiments, the foam member 210 may contain a lubricant, such as a silicone oil, e.g., in the pores of the foam.

Figure 5:
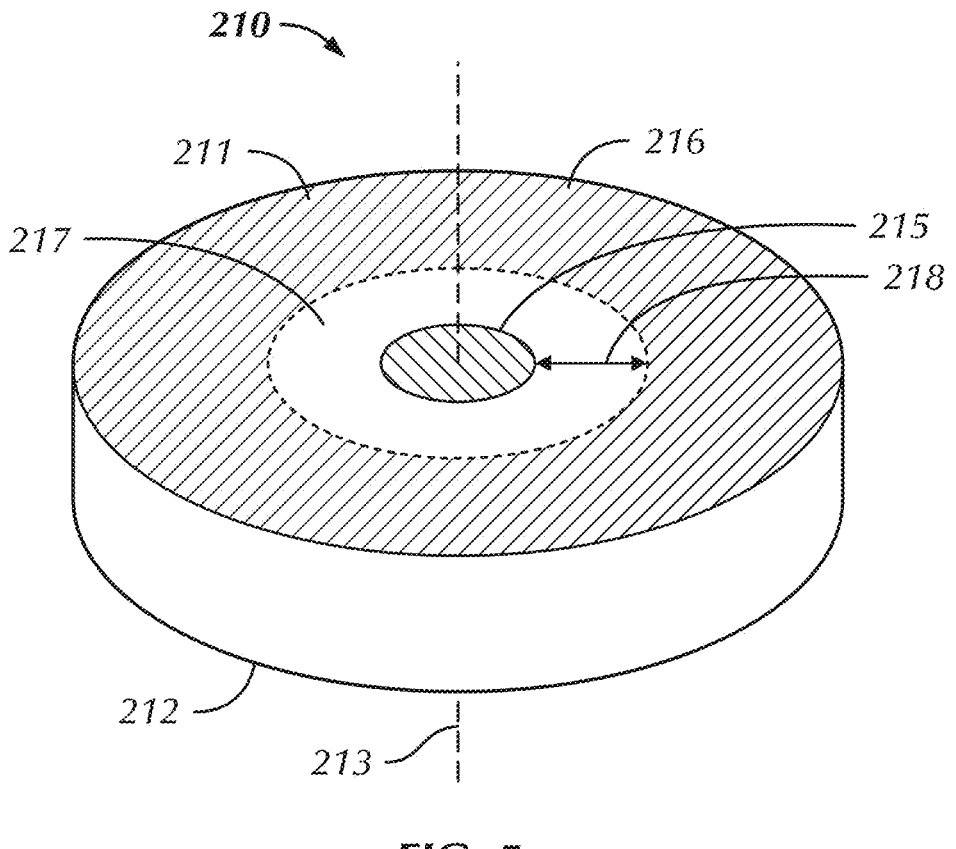
FIG. 5 is an orthogonal representation of an embodiment of a foam member of a hemostatic valve.

Referring to FIG. 5, it can be seen that the foam member 210 has a proximal surface 211 defining a first opening 215 extending along a longitudinal axis 213 from the proximal surface 211 to a distal surface 212 of the foam member 210. In some embodiments, the first opening may be laser cut.

The foam member 210 may have at least one visibly identifiable portion 216 that is distinct from at least one other portion 217 on the proximal surface 211. The at least one visible identifiable portion 216 may be a predetermined distance 218 from at least one edge of the first opening 215.

In some embodiments, the predetermined distance is a distance between 1 mm and 8 mm, such as between 2 mm and 5 mm.

In some embodiments, the at least one visibly identifiable portion may comprise a portion that is visibly darker or lighter than a different portion of the foam. In some embodiments, the at least one visible identifiable portion may comprise one or more additional openings extending at least partially from the proximal surface towards the distal surface. In some embodiments, each of the one or more additional openings may have a diameter less than 0.5 mm. In some embodiments, the one or more additional openings may comprise between 2 and 4 additional openings. In some embodiments, the at least one visible identifiable portion may comprise one or more additional openings extending at least partially from the proximal surface towards the distal surface and a portion that is visibly darker or lighter than a different portion of the foam.

Referring to FIG. 6A, a simplified schematic of an alternative embodiment is seen, where the foam member 300 has an oval-shaped opening 301 and two additional openings 302, each additional opening extending at least partially from the proximal surface towards the distal surface. In FIG. 6A, the two additional openings are shown as being equidistant from an edge of the opening 301.

Referring to FIG. 6B, a simplified schematic of an alternative embodiment is seen, where the foam member 305 has an oval-shaped opening 306 which is surrounded at a distance by the at least one visibly identifiable portion 307 that is darker than a different portion 308 that is closer to the oval-shaped opening 306.

Referring to FIG. 6C, a simplified schematic of an alternative embodiment is seen, where the foam member 315 has an circular opening 316 which is surrounded at different distances by the at least one visibly identifiable portions 312, 313, 314, where each visibly identifiable portion comprises both additional openings 312 each extending at least partially from the proximal surface towards the distal surface, and each additional opening surrounded by a portion 313, 314 that is visibly lighter or darker (here, darker) than a different portion 315 closer to the opening 311. Further, one of the visibly identifiable portions 314 is closer to an edge of the opening 311 than another visible identifiable portion 313.

Referring to FIG. 6D, a simplified schematic of an alternative embodiment is seen, almost an inverse of FIG. 6B. Here, the foam member 329 has a circular opening 321 which is surrounded at a distance by the at least one visibly identifiable portion 322 that is lighter than a different portion 323 that is closer to the oval-shaped opening 321.

In some embodiments, the foam may include more than one piece. In some embodiments, the pieces are adjacent to each other.

Figure 7:
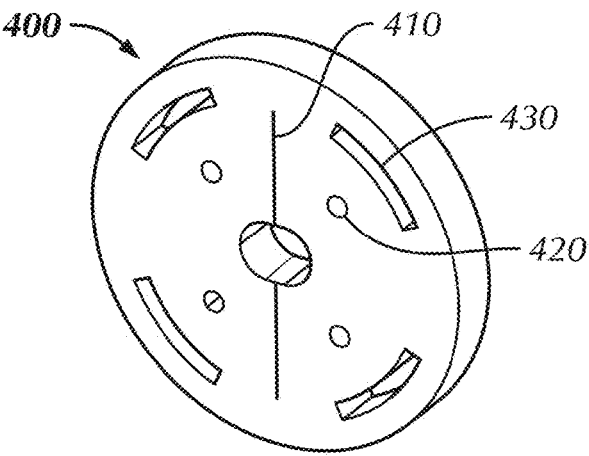
FIG. 7 is a representation of a still another embodiment of a foam member.

Referring to FIG. 7, in some embodiments, there may be cuts 410 (which may be, e.g., slits) in the foam member, extending at least partially, or in some cases entirely, through at least a portion of the foam member. In some embodiments, the cuts may be only in a single direction (e.g., only parallel to the x-axis). In some embodiments, the cuts may extend radially from a central axis. In some embodiments, there be at least one cut that is perpendicular to another cut.

In some embodiments, there may be one or more openings 420 extending through the foam and having a substantially circular cross-section. Such openings are helpful to guide physicians on where to puncture for single access.

In some embodiments, there may one or more openings 430 extending through the foam that do not have a circular cross-section.

In some embodiments, the foam surface facing outward may be divided into quadrants. In some embodiments, each quadrant of the foam may include one or more openings 420.

Figure 8A:
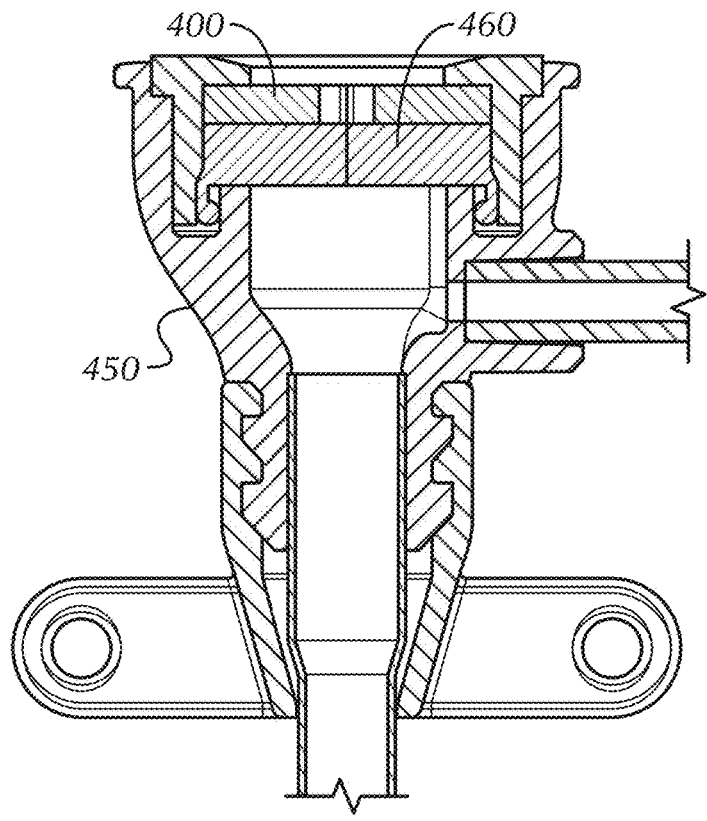
FIGS. 8A and 8B are representations of a foam member in a hub.
Figure 8B:
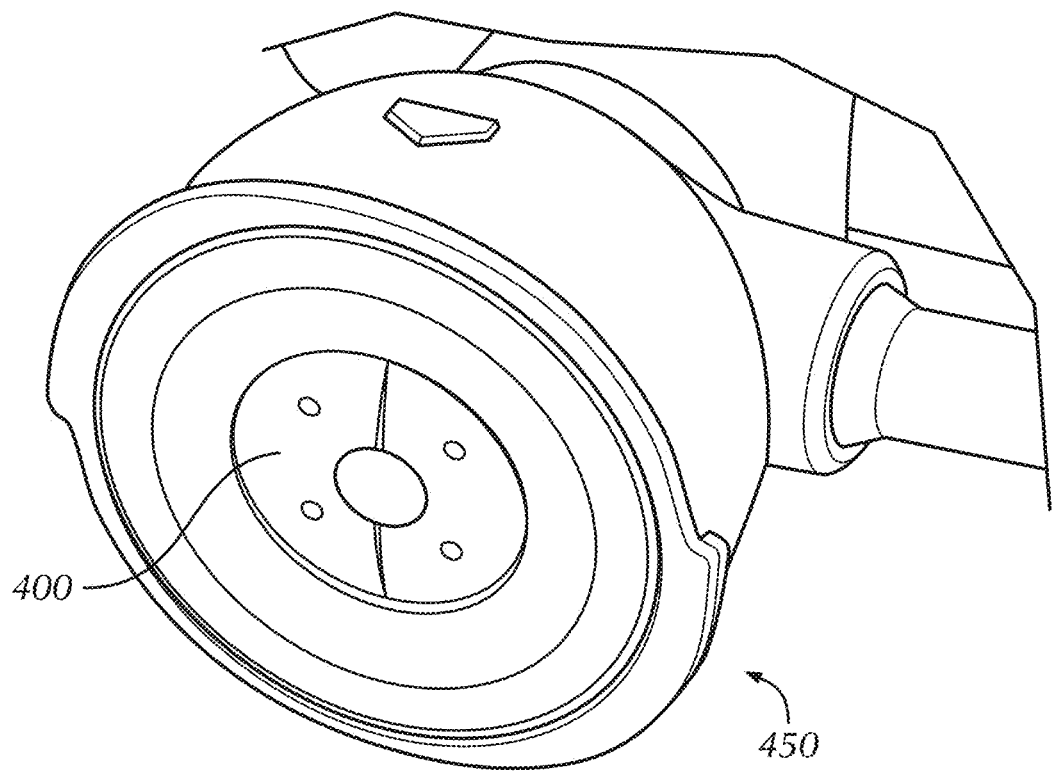

Referring to FIGS. 8A and 8B, a hub 450 can be seen, where the foam member 400 is shown in position within the hub. In some embodiments, a physician may puncture a valve 460 by inserting a needle through one of the openings 420, and through valve 460. In such embodiments, the one or more openings may be guides for aiding the physician in punction the valve.

While various aspects described herein relate to sheath designs that are particularly suitable for simultaneous use with multiple medical devices (e.g., via a single access technique), it should be appreciated that the presently disclosed sheath technology is not limited to uses with multiple medical devices, and that the presently disclosed sheath technology may provide advantages even when used with a single device (e.g., when used only to provide access for an intravascular blood pump or other suitable medical device).

Those skilled in the art will recognize or be able to ascertain using no more than routine experimentation, many equivalents to the specific embodiments of the invention described herein. Such equivalents are intended to be encompassed by the following claims.

What is claimed is:

1. A device for insertion into a vasculature of a patient, the device comprising:

a primary tubular sheath body comprising a first material, the primary tubular sheath body extending from a proximal end to a distal end;

an intermediate tubular sheath body comprising a second material, the intermediate tubular sheath body extending from a proximal end to a distal end, the distal end of the intermediate tubular sheath body connected to the proximal end of the primary tubular sheath body; and a hub comprising a third material, the hub connected to a proximal portion of the intermediate tubular sheath body and separated from the primary tubular sheath body by the intermediate tubular sheath body, wherein the first material, second material, and third material are configured such that a theoretical interfacial bonding strength between the first and second material, and a theoretical interfacial bonding strength between the third material and the second material, are both greater than a theoretical interfacial bonding strength between the first material and the third material.

2. The device according to claim 1, wherein the intermediate tubular sheath body has a first inner diameter at the distal end, and a second inner diameter at an axial distance proximal to the distal end, the second inner diameter being greater than the first inner diameter.

3. The device according to claim 2, wherein the second inner diameter is between 5 mm and 6 mm.

4. The device according to claim 1, wherein the first material comprises a polyether block amide (PEBA).

5. The device according to claim 1, wherein the second material comprises a thermoplastic styrene-butadiene copolymer.

6. The device according to claim 1, wherein the third material comprises acrylonitrile butadiene styrene.

7. The device according to claim 1, wherein the primary tubular sheath body comprises a plurality of layers.

8. The device according to claim 7, wherein the plurality of layers comprises a frame layer and an outer jacket.

9. The device according to claim 8, wherein the frame layer comprises nitinol, and the outer jacket comprises a polyether block amide (PEBA).

10. The device according to claim 1, further comprising a sideport extending from the hub.

11. The device according to claim 1, further comprising a rotatable portion that is rotatable relative to the hub, the primary tubular sheath body, and the intermediate tubular sheath body, the rotatable portion being connected to a distal portion of the hub.

12. The device according to claim 11, wherein the rotatable portion is rotatable by at least 180 degrees.

13. The device according to claim 12, wherein the rotatable portion is rotatable by at least 360 degrees.

14. The device according to claim 11, wherein the rotatable portion is configured to allow a sideport extending from the hub to lie flat against a patient.

15. The device according to claim 11, wherein the rotatable portion comprises a butterfly, a suture pad, or a combination thereof.

* * * * *